United States Patent [19]

Imura

[11] Patent Number: 5,859,709
[45] Date of Patent: Jan. 12, 1999

[54] OPTICAL CHARACTERISTIC MEASURING APPARATUS

[75] Inventor: Kenji Imura, Toyohashi, Japan

[73] Assignee: Minolta Co., Ltd., Osaka, Japan

[21] Appl. No.: 701,579

[22] Filed: Aug. 22, 1996

[30] Foreign Application Priority Data

Aug. 24, 1995 [JP] Japan .................................. 7-215960

[51] Int. Cl.$^6$ .................................................. G01N 21/47
[52] U.S. Cl. .......................... 356/446; 356/236; 250/228
[58] Field of Search ................................... 356/446, 236; 250/228

[56] References Cited

U.S. PATENT DOCUMENTS

| | | | |
|---|---|---|---|
| 4,487,504 | 12/1984 | Goldsmith | 356/323 |
| 4,540,281 | 9/1985 | Akiyama | 356/325 |
| 4,900,923 | 2/1990 | Gerlinger | 250/228 |
| 4,932,779 | 6/1990 | Keane | 356/319 |
| 5,369,481 | 11/1994 | Berg et al. | 356/228 |
| 5,384,641 | 1/1995 | Imura | 356/446 |
| 5,406,367 | 4/1995 | Sopori | 356/30 |

OTHER PUBLICATIONS

Rolf Griesser, "Assessment of Whiteness and Tint of Fluorescent Substrates with Good Interinstrument Correlation," *Color Research and Application*, vol. 19, No. 6, Dec. 1994, pp. 446–460.

J. Anthony Bristow, "The Calibration of Istruments for the Measurement of Paper Whiteness," *Color Research and Application*, vol. 19, No. 6, Dec. 1994, pp. 475–483.

Japanese Industrial Standard, JIS Z 8717—1989, "Methods of Measurement for Colour of Fluorescent Objects".

*Primary Examiner*—F. L. Evans
*Assistant Examiner*—Zandra V. Smith
*Attorney, Agent, or Firm*—Burns, Doane, Swecker & Mathis, LLP

[57] ABSTRACT

An optical characteristic measuring apparatus provided with an integrating sphere measures an optical characteristic of a sample based on an intensity of light from the sample. The apparatus includes the first illuminating system which diffusely illuminates the sample by projecting light to a specified region of the inner surface of the integrating sphere, the second illuminating system which projects light on the sample in such an angle that the light is specularly reflected by the sample to the light measuring system, a storage unit which stores weighting factors in connection with inclusion and exclusion of specular component in the reflection light from the sample, and a calculator which calculates an optical characteristic of the sample based on the measurement data and the weighting factors. The first and second illuminating systems are controlled to operate in a specified sequence.

19 Claims, 4 Drawing Sheets

OPTICAL CHARACTERISTIC MEASURING APPARATUS

BACKGROUND OF THE INVENTION

This invention relates to an apparatus for measuring an optical characteristic of a sample using an integrating sphere, which is adopted in a spectral colorimeter.

In spectral calorimeters or optical characteristic measuring apparatus using an integrating sphere, there are cases of requiring both a spectral reflection coefficient including specular components from a sample (hereinafter, SCI spectral reflection coefficient) and a spectral reflection coefficient excluding specular components (hereinafter, SCE spectral reflection coefficient). For example, for computer color matching (CCM), the SCI data which are unlikely to be influenced by a surface state are often used. For color estimation, etc., the SCE data having a high correlation with visual sense are often used.

In a conventional d/8 optical system which diffusely illuminates a sample by an integrating sphere and receives a reflected light by a light receiving device disposed at 8° with respect to a normal line to a sample surface, a trap aperture is formed at the position of a wall of the integrating sphere that corresponds to −8° with respect to the normal line to the sample surface. This trap aperture is opened and closed to switch specular reflection light incident upon the light receiving device on and off.

Figure 4:
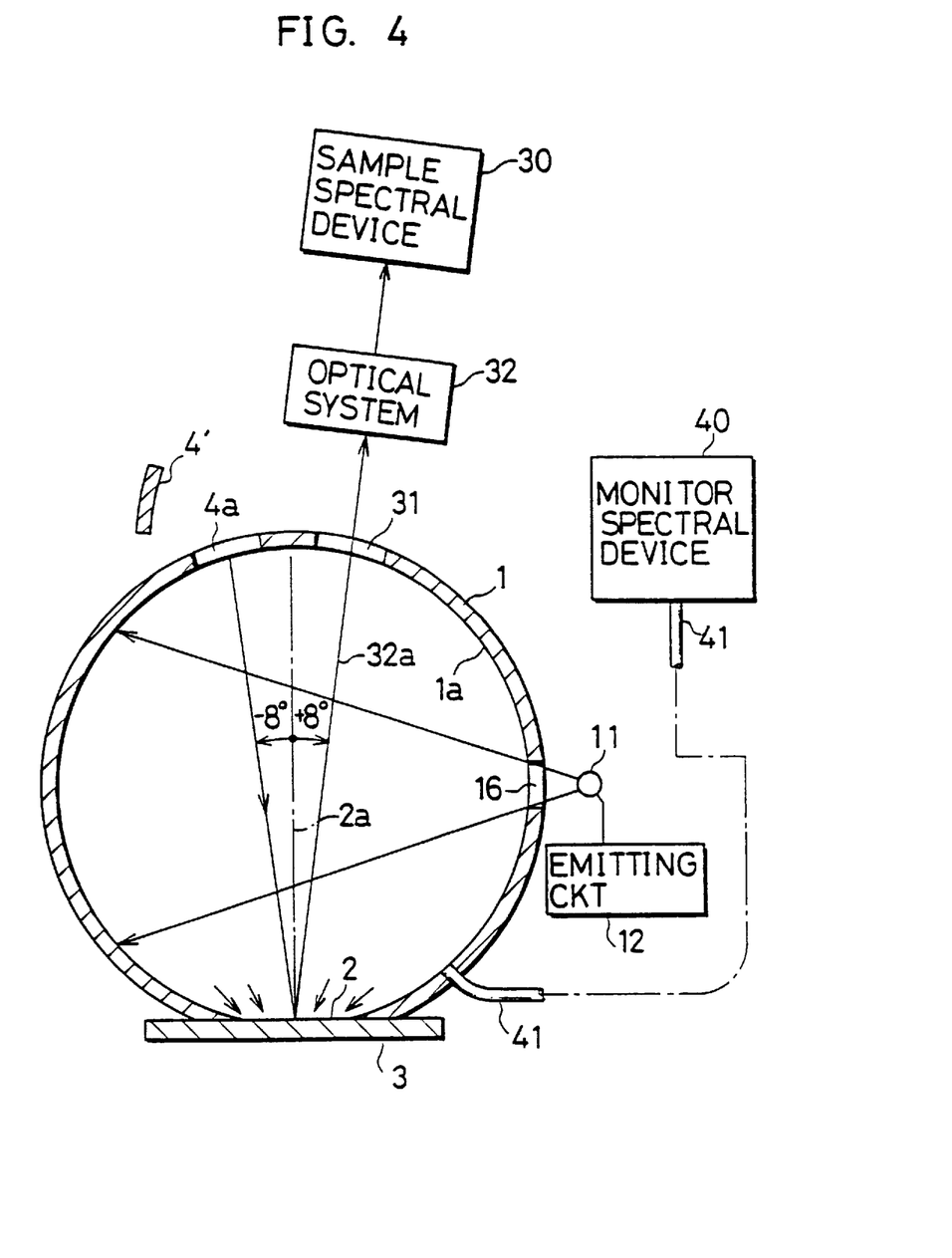
FIG. 4 is a diagram showing a construction of a conventional optical characteristic measuring apparatus.

FIG. 4 shows a conventional optical characteristic measuring apparatus. On an inner surface 1a of an integrating sphere 1 is applied with $BaSO_4$ or the like material having a high diffusion coefficient and a high reflection coefficient. A beam of light from a light source 11 is introduced into the integrating sphere 1 through an aperture 16, undergoes a multiple reflection at the inner surface of the integrating sphere 1, and diffusely illuminates a sample 3 disposed at a sample aperture 2.

The light reflected by the sample 3 is introduced through an aperture 31 to a sample spectral device 30 via a receiving optical system 32. At the same time, a part of the light diffusely illuminating the sample 3 is taken by a light guide 41 and introduced to a monitoring spectral device 40. The reflection coefficient of the sample 3 is calculated based on the outputs of the sample spectral device 30 and the monitoring spectral device 40.

An optical axis 32a of the receiving optical system 32 is slanted by 8° with respect to a normal line 2a of the surface of the sample 3 as shown in FIG. 4. On the other hand, a trap aperture 4a is formed at the position of a wall of the integrating sphere 1 which corresponds to a direction symmetrical to the optical axis 32a of the receiving optical system 32 with respect to the normal line 2a, i.e., along a direction at −8° with respect to the normal line 2a. The trap aperture 4a is selectively closeable by a closing member 4' having a reflective inner surface. In the state that the surface of the sample 3 is smooth, the inner surface of the closing member 4' acts as a light source of the specular reflection light of the sample 3 to be incident upon the receiving optical system 32.

Accordingly, when the closing member 4' is removed as shown in FIG. 4, the SCE spectral reflection coefficient can be measured. On the other hand, when the closing member 4' is placed in the trap aperture 4a, the SCI spectral reflection coefficient can be measured.

However, the conventional apparatus requires a lot of time and labor for the measurement since it makes it necessary to open and close the closing member 4' each time the sample 3 is replaced. In addition, since the conventional apparatus requires such mechanical operation, the reliability of measurement result is inevitably reduced.

SUMMARY OF THE INVENTION

It is an object of the present invention to provide an optical characteristic measuring apparatus which has overcome the problems residing in the prior art.

It is another object of the present invention to provide an optical characteristic measuring apparatus which can have a high reliability and obtain a SCE optical characteristic within a short period of time.

It is still another object of the present invention to provide an optical characteristic measuring apparatus which can have a high reliability and obtain a SCI optical characteristic with high precision within a short period of time.

The present invention is directed to an optical characteristic measuring apparatus comprising: an integrating sphere having an inner surface defining an inside space and a sample aperture where a sample to be measured is placed; a light measuring system which receives light reflected from the sample to produce measurement data in accordance with an intensity of received light; a first illuminating system which diffusely illuminates the sample by projecting light to a specified region of the inner surface of the integrating sphere; a second illuminating system which projects light on the sample in such an angle that the light is specularly reflected by the sample to the light measuring system by projecting light to a specified region of the inner surface of the integrating sphere; a controller which controls the first and second illuminating systems to operate in a specified sequence; a storage unit which stores weighting factors in connection with inclusion and exclusion of specular component in the reflection light from the sample; and a calculator which calculates an optical characteristic of the sample based on the measurement data and the weighting factors.

The weighting factors may include a first correction data for giving weights to measurement data produced when the first illuminating system is operated; and a second weighting factors for giving weights to measurement data produced when the second illuminating system is operated.

The first and second weighting factors each may be those for calculating an optical characteristic of the sample excluding a specular component from the sample. The calculator calculates an optical characteristic of the sample excluding a specular component from the sample.

Also, the first and second weighting factors each may be those for calculating an optical characteristic of the sample including a specular component from the sample. The calculator calculates an optical characteristic of the sample including a specular component from the sample.

Further, the first and second weighting factors each may be those for calculating an optical characteristic of the sample excluding a specular component from the sample and data for calculating an optical characteristic of the sample including a specular component from the sample. The calculator calculates an optical characteristic of the sample excluding a specular component from the sample and an optical characteristic of the sample including a specular component from the sample.

The second illuminating system may be preferably constructed by a light transmittance portion formed in a wall of the integrating sphere, a light source provided outside of the integrating sphere for generating illumination light, a converging member provided outside of the integrating sphere for converging the illumination light into a beam of light, and a reflector provided outside of the integrating sphere for projecting, through the light transmittance portion, the beam of light at the portion of the inner surface of the integrating sphere that intersects an axis symmetrical to an optical axis of the specular reflection light to the light measuring system.

Also, the second illuminating system may be constructed by a translucent window formed in a wall of the integrating sphere, and a light source for generating illumination light, the light source being provided at the position outside of the integrating sphere that intersects an axis symmetrical to an optical axis of the specular reflection light to the light measuring system.

Further, the calculator may be provided with a weighting factor calculating portion for calculating weighting factors based on measurement data for two reference samples having predetermined optical characteristics which are different from each other.

With the thus constructed optical characteristic measuring apparatus, there are provided the first illuminating system which diffusely illuminates the sample and the second illuminating system which projects light on the sample in such an angle that the light is specularly reflected by the sample to the light measuring system. The first and second illuminating systems are operated in a specified sequence. The weighting factors in connection with inclusion and exclusion of specular components is stored in the storage unit. An optical characteristic including or excluding a specular component is produced by changing over the operation of the first and second illuminating systems and executing the calculation based on the measurement data and the weighting factors. Accordingly, the inventive measuring apparatus makes it possible to automatically produce measurement data including specular components and measurement data excluding specular components. Thus, an optical characteristic of a sample including or excluding specular components can be accurately measured for a shorter period of time.

These and other objects, features and advantages of the present invention will become more apparent upon a reading of the following detailed description and accompanying drawings.

DETAILED DESCRIPTION OF THE PREFERRED EMBODIMENT OF THE INVENTION

Figure 1:
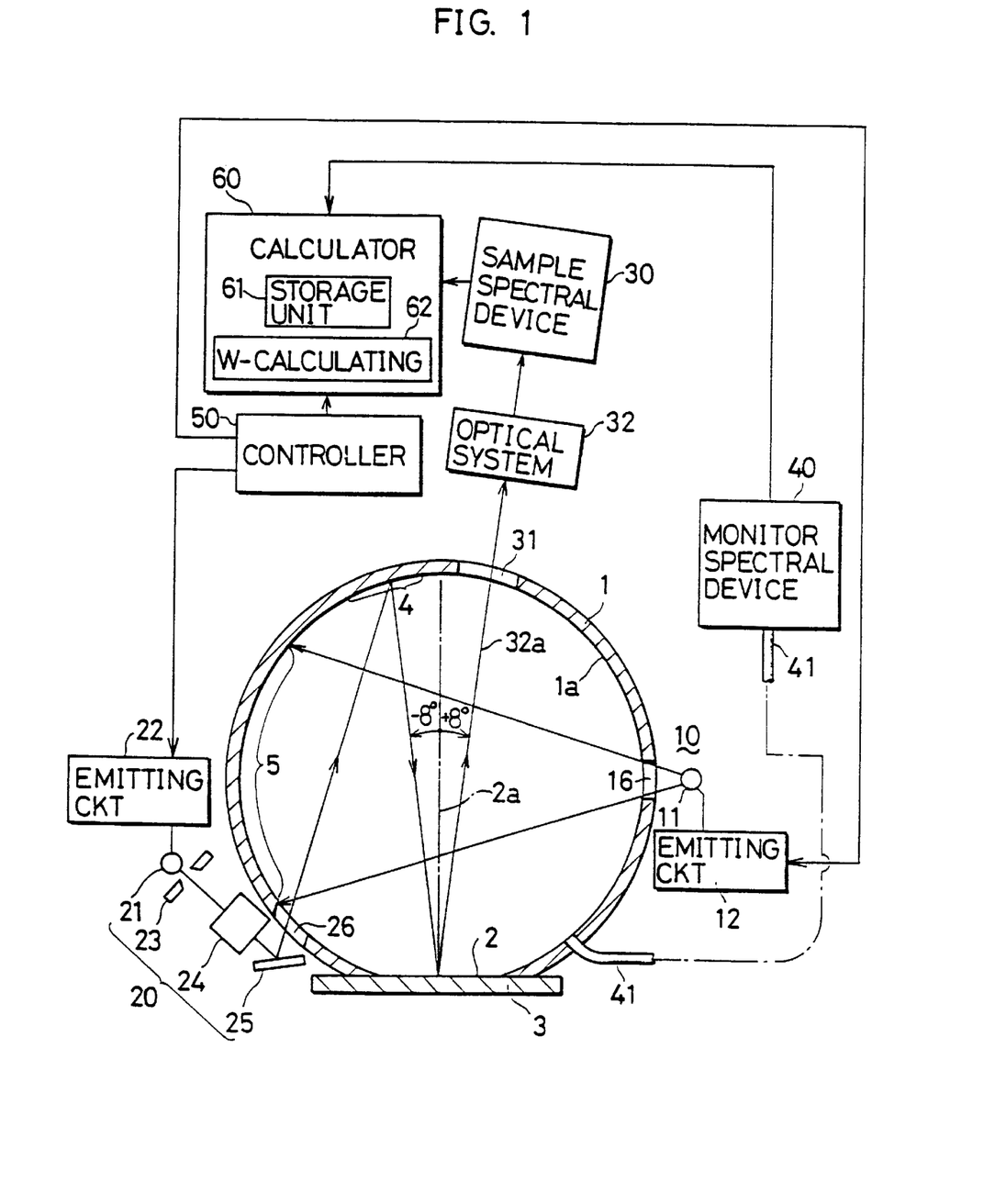
FIG. 1 is a diagram showing a construction of a first optical characteristic measuring apparatus embodying the present invention.

FIG. 1 is a construction diagram of a first optical characteristic measuring apparatus embodying the invention.

An integrating sphere 1 has a hollow sphere. An inner surface 1a of the integrating sphere 1 is applied with a white diffuse reflection paint, such as MgO and $BaSO_4$, having a high diffusion coefficient and a high reflection coefficient. The integrating sphere 1 is formed with a sample aperture 2 where a sample 3 to be measured is placed, and a measurement aperture 31 for allowing reflection light from the sample 3 to be incident upon a receiving optical system 32.

Also, there are provided a first illuminating system 10 and a second illuminating system 20. The first illuminating system includes a light source 11 disposed in the vicinity of the integrating sphere 1, a first light source aperture 16 formed in the integrating sphere 1 for allowing a beam of light from the light source 11 into the integrating sphere 1, and an emitting circuit 12. A xenon flash lamp or the like is used as the light source 11 to supply a beam of light into the integrating sphere 1.

The second illuminating system includes a light source 21, an illumination region restricting plate 23, a converging member 24 and a reflector 25, a second light source aperture 26 formed in the integrating sphere 1 for allowing a beam of light from the light source 21 into the integrating sphere 1, an emitting circuit 22. A xenon flash lamp or the like is used as the light source 21 to supply a beam of light into the integrating sphere 1.

The restricting plate 23 is adapted to restrict the illumination region of the beam from the light source 21. The converging member 24 includes a lens, and is adapted to converge light passed through the restricting plate 23 at the second region 4 of the inner surface 1a of the integrating sphere 1 via the reflector 25.

The receiving optical system 32 includes a lens, and forms a d/8 optical system which is set such that an optical axis 32a is inclined by 8° with respect to a normal axis 2a of the surface of the sample 3. Hence, this optical system 32 receives a reflection light along a direction of 8° from the sample 3. The optical system 32 focuses the received reflection light on entrance aperture of a sample spectral device 30.

The second region 4 is located along a direction of −8° with respect to the normal axis 2a of the surface of the sample 3 and, accordingly, symmetrical to the measurement aperture 31 with respect to the normal axis 2a. Thus, the second region 4 acts as a light source of a specular reflection light which is to be incident upon the receiving optical system 32 from the surface of the sample 3.

When the light source 11 of the first illuminating system 10 is turned on, light is projected onto the first region 5 of the inner surface 1a of the integrating sphere 1. The first region 5 has a large area. The sample 3 is substantially uniformly diffusely illuminated from every direction (see FIG. 2A).

When the light source 21 of the second illuminating system 20 is turned on, a beam of light from the light source 21 is limitedly projected to the second region 4 of the inner surface 1a of the integrating sphere 1. Consequently, the sample 3 is illuminated by a relatively strong beam from the −8° direction to the diffuse illumination light in addition (see FIG. 2B).

The emitting circuits 12, 22 cause the light sources 11, 21 to emit light, respectively, and operate in response to control signals from a controller 50. The sample spectral device 30 measures a spectral intensity of the reflection light of the sample 3, and the obtained measurement data is sent to a calculator 60.

A light guide 41 is mounted on the integrating sphere 1. The light guide 41 is made of an optical fiber or the like material, and introduces a part of the illumination light in the integrating sphere 1, which is incident upon an incident end, to the monitoring spectral device 40. The monitoring spectral device 40 monitors a spectral intensity of the illumination light, and the obtained data is sent to the calculator 60.

The controller 50 includes a CPU and memories storing a control program, and controls the operation of the optical characteristic measuring apparatus in accordance with the control program. For example, the controller 50 controllably turns on and off the light sources 11, 21 via the emitting circuits 12, 22.

The calculator 60 includes a storage unit 61 for storing weighting factors for data correction. Weighting factors will be described later. The calculator calculates SCI and SCE reflection characteristics of the sample 3 based on measurement data from the sample spectral device 30 and the monitoring spectral device 40 using weighting factors stored in the storage unit 61.

Further, the calculator 60 is provided with a weighting factor calculating function 62 to calculate weighting factors from obtained measurement data. The weighting factor calculation will be described later in more detail. Before each measurement or every several measurements, weighting factors are calculated by the calculating function 62 and stored in the storage unit 61 to ensure accurate measurement.

However, it may not be necessary to calculate weighting factors frequently because weighting factors are dependent on the structure of the optical system and not likely to vary in the lapse of time. For example, weighting factors are calculated once at the time when the apparatus is completed and stored in the storage unit 61 permanently. In this case, the weighting factor calculating function 62 is not required to be provided in the calculator 60.

Figure 2A:
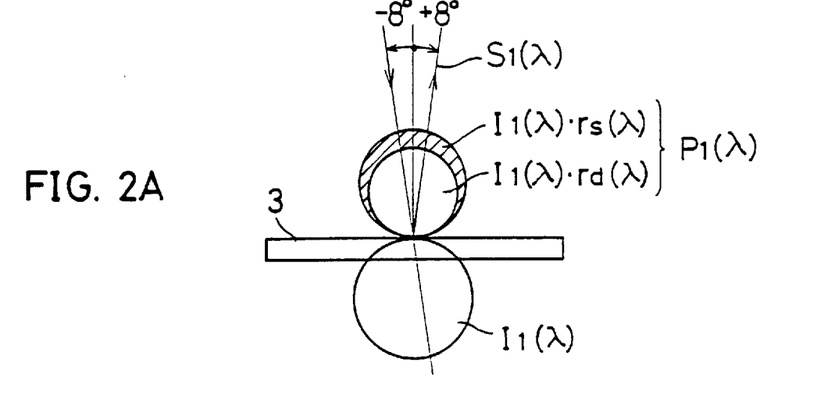
FIGS. 2A to 2C are diagrams showing angular distributions, FIG. 2A showing angular distributions of an illumination light of an integrating sphere of the apparatus and reflection light from a sample under the first measurement condition, FIG. 2B showing angular distributions of the illumination light of the integrating sphere and reflection light from the sample under the second measurement condition, and FIG. 2C showing angular distributions of an illumination light $I_c(\lambda)$ and a reflection light $S_c(\lambda)$ from the sample under a SCE illumination condition.
Figure 2B:
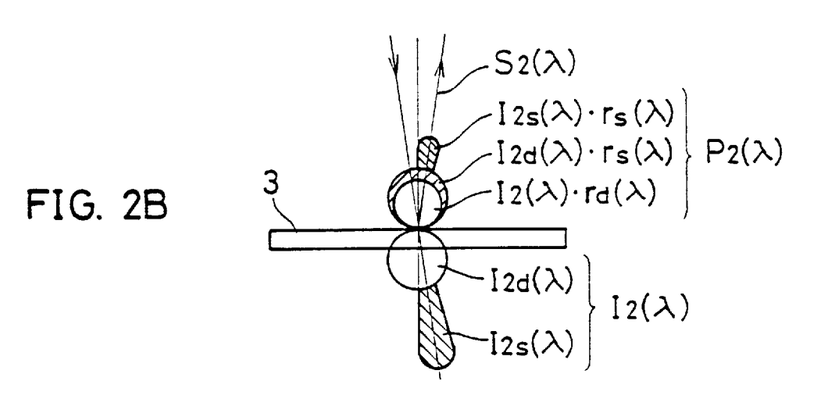
Figure 2C:
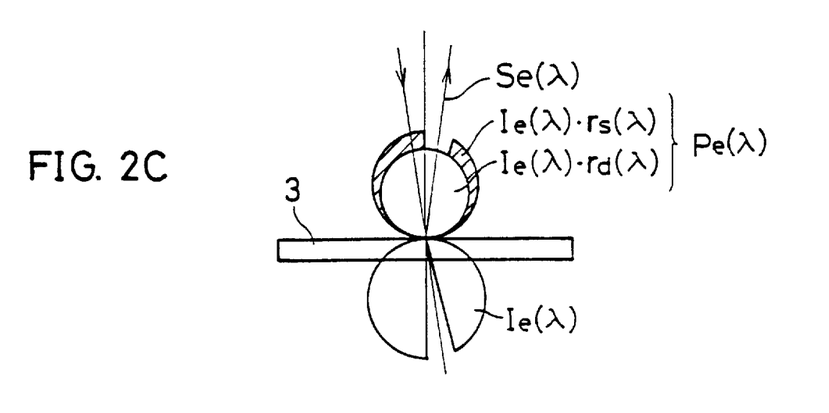

Next, a measurement principle is described with respect to a wavelength component $\lambda$ with reference to FIGS. 2A to 2C. In these figures, $I(\lambda)$, $P(\lambda)$, $S(\lambda)$ denote illumination light, reflection light from the sample 3, and light received by the sample spectral device 30 via the measurement aperture 31 out of the reflection light $P(\lambda)$, respectively.

FIG. 2A shows angular distributions of the illumination light of the integrating sphere 1 and the reflection light from the sample 3 under the first measurement condition, i.e., when the light source 11 is turned on.

In this case, the illumination light $I_1(\lambda)$ is diffused. If $r_s(\lambda)$ and $r_d(\lambda)$ denote the specular reflection coefficient and diffused reflection coefficient of the sample 3, respectively, the reflection light $P_1(\lambda)$ is a sum of the diffused reflection light $I_1(\lambda) \cdot r_d(\lambda)$ and the specular reflection light $I_1(\lambda) \cdot r_s(\lambda)$.

Since the illumination light $I_1(\lambda)$ is diffused, the diffused reflection light $I_1(\lambda) \cdot r_d(\lambda)$ and the specular reflection light $I_1(\lambda) \cdot r_s(\lambda)$ also are diffused, and components $S_1(\lambda)$ of 8° direction of the reflection light $P_1(\lambda)$ are received. At this time, an apparent reflection coefficient $r_1(\lambda)$ is calculated in accordance with Equation (1).

$$\begin{aligned} r_1(\lambda) &= S_1(\lambda)/I_1(\lambda) \quad &\text{[Equation 1]} \\ &= K(\lambda) \cdot \{I_1(\lambda) \cdot r_d(\lambda) + I_1(\lambda) \cdot r_s(\lambda)\}/I_1(\lambda) \\ &= K(\lambda) \cdot r_d(\lambda) + K(\lambda) \cdot r_s(\lambda) \end{aligned}$$

In Equation (1), $K(\lambda)$ is a constant representing a ratio of the light received by the sample spectral device 30 to all the diffused reflection light and determined by the structure of the optical system including the integrating sphere 1 and the receiving optical system 32 of the measuring apparatus, and $K(\lambda) \ll 1$.

FIG. 2B shows angular distributions of the illumination light of the integrating sphere 1 and the reflection light from the sample 3 under the second measurement condition, i.e., when the light source 21 is turned on.

In this case, an illumination light $I_2(\lambda)$ is comprised of a directional light $I_{2s}(\lambda)$ of −8° direction for directly illuminating the sample 3 from the second region 4 and a diffused light $I_{2d}(\lambda)$ illuminating other portion of the inner surface 1a from the second region 4 and illuminating the sample 3 after being reflected by the inner surface 1a many times. The illumination light $I_2(\lambda)$ is expressed: $I_2(\lambda) = I_{2s}(\lambda) + I_{2d}(\lambda)$ At this time, the reflection light $P_2(\lambda)$ is comprised of a diffused reflection light $I_2(\lambda) \cdot r_d(\lambda)$ of the illumination light $I_2(\lambda)$, a specular reflection light $I_{2d}(\lambda) \cdot r_s(\lambda)$ of the diffused light $I_{2d}(\lambda)$, and a specular reflection light $I_{2s}(\lambda) \cdot r_s(\lambda)$ of the directional light $I_{2s}(\lambda)$.

Among these reflection lights, $I_2(\lambda) \cdot r_d(\lambda)$ and $I_{2d}(\lambda) \cdot r_s(\lambda)$ are diffusive because $r_d(\lambda)$ has diffusivity, and 8° direction components thereof are received. On the other hand, $I_{2s}(\lambda) \cdot r_s(\lambda)$ is entirely received because it has directivity and, accordingly, has a large contribution to an apparent reflection coefficient $r_2(\lambda)$. At this time, the apparent reflection coefficient $r_2(\lambda)$ is obtained in accordance with Equation (2).

$$\begin{aligned} r_2(\lambda) &= S_2(\lambda)/I_2(\lambda) \quad &\text{[Equation 2]} \\ &= K(\lambda)\{I_2(\lambda) \cdot r_d(\lambda) + I_{2d}(\lambda) \cdot r_s(\lambda)\}/I_2(\lambda) + \\ &\quad I_{2s}(\lambda) \cdot r_s(\lambda)/I_2(\lambda) \\ &= K(\lambda) \cdot r_d(\lambda) + \{K(\lambda) \cdot I_{2d}(\lambda) + I_{2s}(\lambda)\}/I_2(\lambda) \cdot r_s(\lambda) \end{aligned}$$

FIG. 2C shows angular distributions of the illumination light and the reflection light from the sample 3 under a SCE illumination condition.

An illumination light $I_c(\lambda)$ is diffused similar to the illumination light of FIG. 2A, but lacks −8° direction components.

Similar to the reflection light of FIG. 2A, a reflection light $P_c(\lambda)$ is composed of a diffused reflection light $I_c(\lambda) \cdot r_d(\lambda)$ and a specular reflection light $I_c(\lambda) \cdot r_s(\lambda)$. However, since the illumination light $I_c(\lambda)$ lacks the −8° direction components, the specular reflection light $I_c(\lambda) \cdot r_s(\lambda)$ lacks 8° direction components. When the reflection light $P_e(\lambda)$ is received from the direction of 8°, an apparent reflection coefficient $r_e(\lambda)$ is calculated in accordance with Equation (3).

$$\begin{aligned} r_e(\lambda) &= S_e(\lambda)/I_e(\lambda) \quad &\text{[Equation 3]} \\ &= K(\lambda) \cdot I_e(\lambda) \cdot r_d(\lambda)/I_e(\lambda) \\ &= K(\lambda) \cdot r_d(\lambda) \end{aligned}$$

A SCI illumination condition is same as in the case of FIG. 2A, and an apparent reflection coefficient $r_i(\lambda)$ under this condition is calculated in accordance with Equation (4).

$$\begin{aligned} r_i(\lambda) &= r_1(\lambda) \quad &\text{[Equation 4]} \\ &= K(\lambda) \cdot r_d(\lambda) + K(\lambda) \cdot r_s(\lambda) \end{aligned}$$

More specifically, as shown in Equations (1) to (4) the apparent reflection coefficients $r_1(\lambda)$, $r_2(\lambda)$ under the first and second measurement conditions and the apparent reflection coefficients $r_i(\lambda)$, $r_e(\lambda)$ under the SCI and SCE illumination conditions are expressed as a linear combination of the diffused reflection coefficient $r_d(\lambda)$ and the specular reflection coefficient $r_s(\lambda)$ peculiar to the sample 3.

It should be noted that the factor $\{K(\lambda) \cdot I_{2d}(\lambda) + I_{2s}(\lambda)\}$ of the term $r_s(\lambda)$ of Equation (2) is a constant determined by the optical system.

[Equation 5]

$$r_i(\lambda) = a_1(\lambda) \cdot r_1(\lambda) + a_2(\lambda) \cdot r_2(\lambda)$$

[Equation 6]

$$r_e(\lambda) = b_1(\lambda) \cdot r_1(\lambda) + b_2(\lambda) \cdot r_2(\lambda)$$

Accordingly, the apparent reflection coefficients $r_i(\lambda)$, $r_e(\lambda)$ under the SCI and SCE illumination conditions are expressed as a linear combination of the apparent reflection coefficients $r_1(\lambda)$, $r_2(\lambda)$ under the first and second measurement conditions by using suitable factors $a_1(\lambda)$, $a_2(\lambda)$, $b_1(\lambda)$ and $b_2(\lambda)$.

Next, illumination light data monitored by the monitoring spectral device 40 is described.

Between the illumination lights $I_1(\lambda)$, $I_2(\lambda)$, $I_{2d}(\lambda)$ and $I_{2s}(\lambda)$ and output data $M_1(\lambda)$ and $M_2(\lambda)$ obtained by measuring a part of the illumination light incident upon the light guide 41 by the monitoring spectral device 40 under the first and second measurement conditions, there are relationships as defined in Equations (7) and (8).

[Equation 7]

$$I_1(\lambda) = c_1(\lambda) \cdot M_1(\lambda)$$

[Equation 8]

$$I_2(\lambda) = c_2(\lambda) \cdot M_2(\lambda)$$

$$I_{2d}(\lambda) = c_{2d}(\lambda) \cdot M_2(\lambda)$$

$$I_{2s}(\lambda) = c_{2s}(\lambda) \cdot M_2(\lambda)$$

Here, $c_1(\lambda)$, $c_2(\lambda)$, $c_{2d}(\lambda)$ and $C_{2s}(\lambda)$ are constants determined by the optical system. By using Equations (1), (2), (7) and (8), even if $I_1(\lambda)$, $I_2(\lambda)$, $I_{2d}(\lambda)$ and $I_{2s}(\lambda)$ are replaced by measurable $M_1(\lambda)$ and $M_2(\lambda)$, it can be still held that the apparent reflection coefficients $r_1(\lambda)$, $r_2(\lambda)$ be a linear combination of the diffused reflection coefficient $r_d(\lambda)$ and the specular reflection coefficient $r_s(\lambda)$. In this case, Equations (5) and (6) also hold.

Next, reflection coefficient correction for correcting the apparent reflection coefficients $r_i(\lambda)$, $r_e(\lambda)$ into real reflection coefficients $R_i(\lambda)$, $R_e(\lambda)$ is described.

The real reflection coefficients $R_i(\lambda)$, $R_e(\lambda)$ can be expressed as follows using the apparent reflection coefficients $r_i(\lambda)$, $r_e(\lambda)$.

[Equation 9]

$$R_i(\lambda) = C_i(\lambda) \cdot r_i(\lambda)$$

[Equation 10]

$$R_e(\lambda) = C_e(\lambda) \cdot r_e(\lambda)$$

where $C_i(\lambda)$, $C_e(\lambda)$ are constants determined by the optical system.

Accordingly, the real reflection coefficients $R_i(\lambda)$, $R_e(\lambda)$ can be expressed as follows using new weighting factors $A_1(\lambda)$, $A_2(\lambda)$, $B_1(\lambda)$, $B_2(\lambda)$ taking Equations (5) to (10) in account. These weighting factors are used as the correction data.

[Equation 11]

$$R_i(\lambda) = A_1(\lambda) \cdot r_1(\lambda) + A_2(\lambda) \cdot r_2(\lambda)$$

[Equation 12]

$$R_e(\lambda) = B_1(\lambda) \cdot r_1(\lambda) + B_2(\lambda) \cdot r_2(\lambda)$$

The SCI reflection coefficient can be obtained based on the first weighting factor $A_1(\lambda)$ and the second weighting factor $A_2(\lambda)$ for SCI reflection coefficient. The SCE reflection coefficient can be obtained based on the first weighting factor $B_1(\lambda)$ and the second weighting factor $B_2(\lambda)$ for SCE reflection coefficient.

Next, a procedure of obtaining the weighting factors $A_1(\lambda)$, $A_2(\lambda)$ and $B_1(\lambda)$, $B_2(\lambda)$ is described.

The weighting factors $A_1(\lambda)$, $A_2(\lambda)$ and $B_1(\lambda)$, $B_2(\lambda)$ are constants peculiar to the optical system, and can be obtained by measuring two reference samples having known SCI and SCE spectral reflection coefficients which are different from each other.

Here, the SCI and SCE reflection coefficients of two reference samples Sa, Sb are assumed to be $Ra_i(\lambda)$, $Rb_i(\lambda)$, respectively. By measuring these two reference samples Sa, Sb under the first and second measurement conditions, apparent reflection coefficients $ra_1(\lambda)$, $rb_1(\lambda)$ and $ra_2(\lambda)$, $rb_2(\lambda)$ are obtained.

From Equation (11), there are relationships as defined in Equations (13) and (14) between the above values.

[Equation 13]

$$Ra_i(\lambda) = A_1(\lambda) \cdot ra_1(\lambda) + A_2(\lambda) \cdot ra_2(\lambda)$$

[Equation 14]

$$Rb_i(\lambda) = A_1(\lambda) \cdot rb_1(\lambda) + A_2(\lambda) \cdot rb_2(\lambda)$$

Further, from Equation (12), there are relationships as defined in Equations (15) and (16) between the above values.

[Equation 15]

$$Ra_e(\lambda) = B_1(\lambda) \cdot ra_1(\lambda) + B_2(\lambda) \cdot ra_2(\lambda)$$

[Equation 16]

$$Rb_e(\lambda) = B_1(\lambda) \cdot rb_1(\lambda) + B_2(\lambda) \cdot rb_2(\lambda)$$

The first and second weighting factors $A_1(\lambda)$, $A_2(\lambda)$ for SCI reflections coefficients can be obtained by solving the simultaneous Equations (13), (14), whereas the first and second weighting factors $B_1(\lambda)$, $B_2(\lambda)$ for SCE reflection coefficient can be obtained by solving the simultaneous Equations (15), (16).

Since the first measurement condition is same as the SCI illumination condition, $A_2(\lambda) = 0$ may be set. However, since the optical system of a reference measuring apparatus providing the reference reflection coefficients $Ra_i(\lambda)$, $Rb_i(\lambda)$ cannot completely agree with the optical system of the measuring apparatus actually used, it is better to calculate $A_2(\lambda)$ in accordance with Equations (13), (14) on the assumption that $A_2(\lambda) \neq 0$. In this way, the SCI reflection coefficient more approximate to that of the reference measuring apparatus can be obtained, and highly accurate measurement data can be obtained.

Next, a measurement procedure of this optical characteristic measuring apparatus is described.

First, the controller 50 causes the emitting circuit 12 to operate, and then light is emitted from the light source 11 and illuminates the sample 3 placed at the sample aperture 2 of the integrating sphere 1 under the first measurement condition shown in FIG. 2A. A spectral data $S_1(\lambda)$ of the reflection light of the sample 3 and a spectral data $M_1(\lambda)$ of the illumination light are input to the calculator 60 from the sample spectral device 30 and the monitoring spectral device 40. The apparent reflection coefficient $r_1(\lambda)$ is calculated: $r_1(\lambda) = S_1(\lambda)/M_1(\lambda)$.

Subsequently, the emitting circuit 22 operates, and the light is emitted from the light source 21 to illuminate the sample 3 under the second illumination condition shown in FIG. 2B. Similar to the above, the apparent reflection is calculated: $r_2(\lambda)=S_2(\lambda)/M_2(\lambda)$.

Two reference samples having known SCI and SCE reflection coefficients which are different from each other are placed at the sample aperture 2 of the integrating sphere 1 to make measurements under the first and second measurement conditions in advance. The coefficients $A_1(\lambda)$, $A_2(\lambda)$ and $B_1(\lambda)$, $B_2(\lambda)$ are obtained based on the measurement results, and are stored in the storage unit 61 of the calculator 60.

Thereafter, a general sample is placed at the sample aperture 2 as a sample 3, and measurements under the first and second measurement conditions are made to obtain the apparent reflection coefficients $r_1(\lambda)$, $r_2(\lambda)$. Then, the real reflection coefficients $R_1(\lambda)$, $R_e(\lambda)$ are obtained in accordance with Equations (11), (12) using the stored factors $A_1(\lambda)$, $A_2(\lambda)$ $B_1(\lambda)$ and $B_2(\lambda)$.

In this way, the measurement data under the SCE illumination condition can be obtained without forming a trap aperture in an integrating sphere 1 which is required in the conventional apparatus. Also, no mechanical operation is required for SCI, SCE measurements. Accordingly, the accuracy of measurement data can be remarkably improved and the high measurement reliability can be thus maintained over a long term.

Further, since the measurements under the first and second measurement conditions are actually completed within several tens of milliseconds, the measurement time can be remarkably shortened as compared with the measurement associated with the mechanical opening and closing of the trap aperture in the conventional apparatus.

Figure 3:
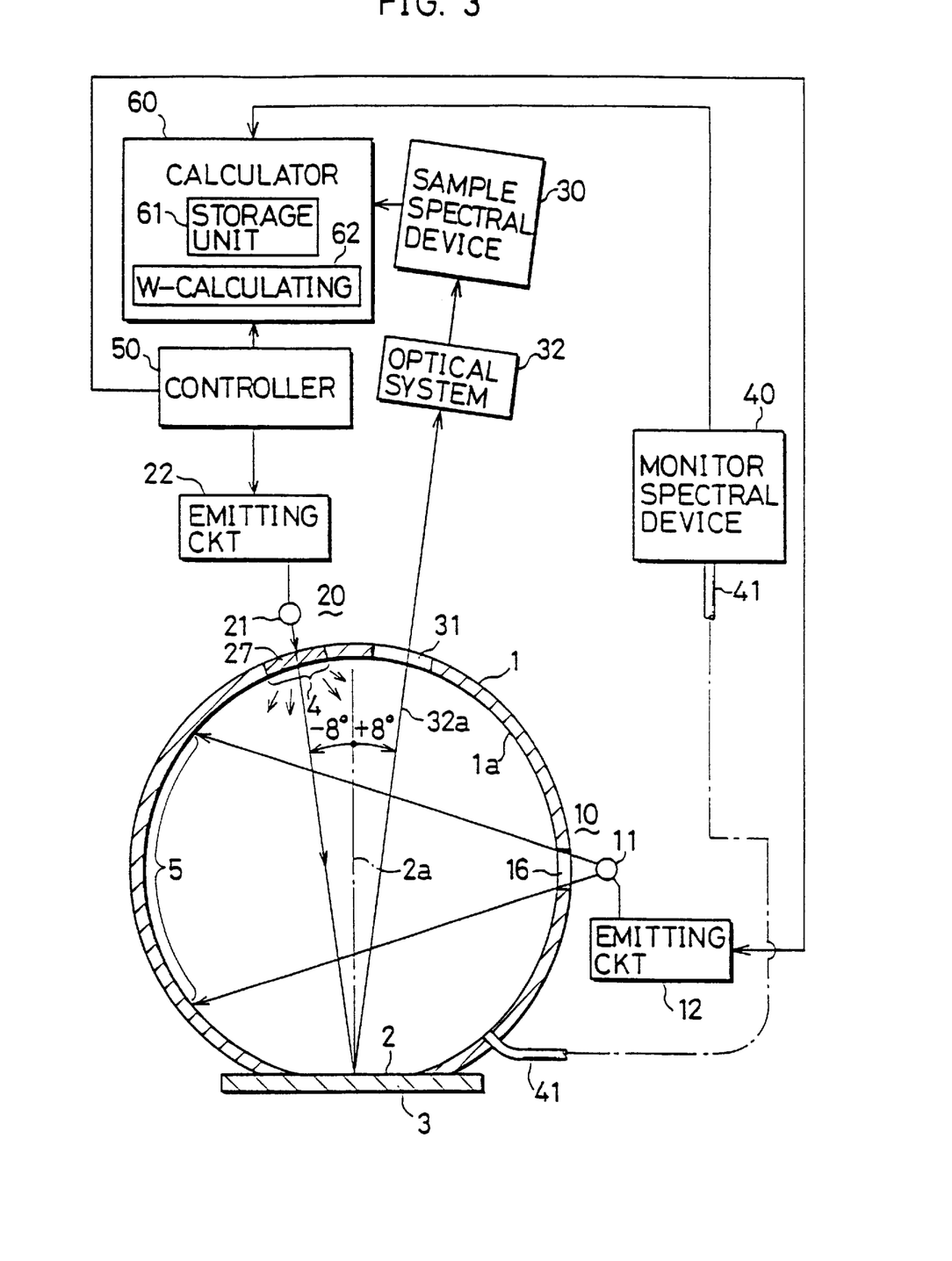
FIG. 3 is a diagram showing a construction of the second optical characteristic measuring apparatus embodying the present invention.

FIG. 3 is a diagram showing a construction of a second optical characteristic measuring apparatus of the invention. No description is given to elements identical to those of the first embodiment by identifying them by the same reference numerals.

In the second embodiment, a second region 4 of an integrating sphere 1 is covered with a translucent window 27 capable of diffusely transmitting light. A light source 21 and the transmitter 27 constitutes a second illuminating system 20 of the second apparatus. Under a second measurement condition, a light source 21 is turned on and a beam of light is then introduced into the integrating sphere 1 through the second region 4. The introduced beam is used as a light source for the specular reflection light of the sample 3 to be incident upon a receiving optical system 32.

In the thus constructed second embodiment, a part of the beam escapes outside the integrating sphere 1 because of the second region 4 having diffuse transmissivity. Accordingly, the diffuseness of the illumination light is slightly reduced as compared with the first embodiment. However, Equations (11), (12) in principle hold. Thus, reliable measurement can be made in the same manner as in the first embodiment, and the same advantages as the first embodiment can be obtained.

In the foregoing embodiments, measurement of reflection characteristic of a sample is described. However, the present invention may be applicable for measurement of transmittance of a sample.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. An optical characteristic measuring apparatus comprising:

an integrating sphere having an inner surface defining an inside space and a sample aperture where a sample to be measured is placed;

a light measuring system which receives light reflected from the sample to produce measurement data in accordance with an intensity of received light;

a first illuminating system which diffusely illuminates the sample by projecting light to a specified region of the inner surface of the integrating sphere;

a second illuminating system which projects light on the sample in such an angle that the light specularly reflected by the sample is directed to the light measuring system;

a controller which controls the first and second illuminating systems to operate in a specified sequence;

a storage unit which stores weighting factors in connection with inclusion and exclusion of specular component in the reflection light from the sample; and a calculator which calculates an optical characteristic of the sample based on the measurement data and the weighting factors wherein the weighting factors includes:

first weighting factors for giving weight to measurement data produced when the first illuminating system is operated; and second weighting factors for giving weight to measurement data produced when the second illuminating system is operated.

2. An optical characteristic measuring apparatus as defined in claim 1, wherein:

the first and second weighting factors each including data for calculating an optical characteristic of the sample excluding a specular component from the sample; and the calculator is operable to calculate an optical characteristic of the sample excluding a specular component from the sample.

3. An optical characteristic measuring apparatus as defined in claim 2, wherein the optical characteristic calculated by the calculator is a spectral reflectance of the sample.

4. An optical characteristic measuring apparatus as defined in claim 1, wherein:

the first and second weighting factors each including data for calculating an optical characteristic of the sample including a specular component from the sample; and the calculator is operable to calculate an optical characteristic of the sample including a specular component from the sample.

5. An optical characteristic measuring apparatus as defined in claim 4, wherein the optical characteristic calculated by the calculator is a spectral reflectance of the sample.

6. An optical characteristic measuring apparatus as defined in claim 1, wherein:

the first and second weighting factors each including:
data for calculating an optical characteristic of the sample excluding a specular component from the sample
data for calculating an optical characteristic of the sample including a specular component from the sample; and the calculator is operable to calculate an optical characteristic of the sample excluding a specular component from the sample and an optical characteristic of the sample including a specular component from the sample.

7. An optical characteristic measuring apparatus as defined in claim 6, wherein the optical characteristic calculated by the calculator is a spectral reflectance of the sample.

8. An optical characteristic measuring apparatus as defined in claim 1, wherein the second illuminating system includes:
   a light transmittance portion formed in a wall of the integrating sphere;
   a light source provided outside of the integrating sphere for generating illumination light;
   a converging member provided outside of the integrating sphere for converging the illumination light into a beam of light and projecting, through the light transmittance portion, the beam of light at the portion of the inner surface of the integrating sphere that intersects an axis symmetrical to an optical axis of the specular reflection light to the light measuring system.

9. An optical characteristic measuring apparatus as defined in claim 8, wherein the transmittance portion is defined by an aperture formed in the wall of the integrating sphere.

10. An optical characteristic measuring apparatus as defined in claim 1, wherein the second illuminating system includes:
    a light transmittance portion formed at the position of wall of the integrating sphere that intersects an axis symmetrical to an optical axis of the specular reflection light to the light measuring system; and
    a light source for generating illumination light, the light source being provided at the position outside of the light transmittance portion.

11. An optical characteristic measuring apparatus as defined in claim 10, wherein the transmittance portion is defined by a translucent member formed in the wall of the integrating sphere.

12. An optical characteristic measuring apparatus comprising:
    an integrating sphere having an inner surface defining an inside space and a sample aperture where a sample to be measured is placed;
    a light measuring system which receives light reflected from the sample to produce measurement data in accordance with an intensity of received light;
    a first illuminating system which diffusely illuminates the sample by projecting light to a specified region of the inner surface of the integrating sphere;
    a second illuminating system which projects light on the sample in such an angle that the light specularly reflected by the sample is directed to the light measuring system;
    a controller which controls the first and second illuminating systems to operate in a specified sequence;
    a storage unit which stores weighting factors in connection with inclusion and exclusion of specular component in the reflection light from the sample; and
    a calculator which calculates an optical characteristic of the sample based on the measurement data and the weighting factors wherein the calculator includes a weighting factor calculating portion for calculating weighting factors based on measurement data for a plurality of reference samples having predetermined optical characteristics which are different from each other.

13. An optical characteristic measuring apparatus comprising:
    an integrating sphere having an inner surface defining an inside space and a sample aperture where a sample to be measured is placed;
    a light measuring system which receives light reflected from the sample to produce measurement data in accordance with an intensity of received light;
    a first illuminating system which supplies illumination light into the inside space of the integrating sphere so that the light measuring system substantially receives diffuse reflection light from the sample;
    a second illuminating system which supplies illumination light having a directivity into the inside space of the integrating sphere so that the light measuring system substantially receives specular reflection light from the sample; and
    a calculator which calculates a first optical characteristic of the sample including a specular component and a second optical characteristic of the sample excluding a specular component based on a first measurement data obtained when the first illuminating system is activated and a second measurement data obtained when the second illuminating system is activated.

14. An optical characteristic measuring apparatus as defined in claim 13, wherein the second illuminating system projects the illumination light having a directivity to a specified region of the inner surface of the integrating sphere so that reflection light from the specified region falls on the sample at such an angle as to cause specular reflection light to the light measuring system.

15. An optical characteristic measuring apparatus as defined in claim 13, wherein the second illuminating system projects the illumination light having a directivity directly on the sample at such an angle as to cause specular reflection light to the measuring system.

16. An optical characteristic measuring apparatus as defined in claim 15, wherein the second illuminating system projects the illumination light having a directivity on the sample through a light transmittance portion formed in a wall of the integrating sphere.

17. An optical characteristic measuring apparatus as defined in claim 13, further comprising a memory which stores a plurality of weighting factors, wherein the calculator multiplies first and second measurement data and the plurality of weighting factors respectively to obtain first and second optical characteristics of the sample.

18. An optical characteristic measuring apparatus as defined in claim 17, wherein the plurality of weighting factors are calculated based on measurement data for a plurality of reference samples each having a predetermined first optical characteristic including a specular component, and a predetermined second optical characteristic excluding a specular component, the predetermined first and second optical characteristics of the plurality of reference samples being different from one another.

19. An optical characteristic measuring apparatus as defined in claim 13, wherein the first and second optical characteristics are spectral reflectances.

* * * * *